US012396752B2

(12) United States Patent
Byager

(10) Patent No.: US 12,396,752 B2
(45) Date of Patent: Aug. 26, 2025

(54) INSERTER SYSTEM WITH TRANSPORT PROTECTION

(71) Applicant: UnoMedical A/S, Birkerød (DK)

(72) Inventor: Rune Frimand Byager, Frederiksberg (DK)

(73) Assignee: Unomedical A/S, Birkerød (DK)

(*) Notice: Subject to any disclaimer, the term of this patent is extended or adjusted under 35 U.S.C. 154(b) by 125 days.

(21) Appl. No.: 17/667,978

(22) Filed: Feb. 9, 2022

(65) Prior Publication Data

US 2022/0160396 A1 May 26, 2022

Related U.S. Application Data

(63) Continuation of application No. 16/265,832, filed on Feb. 1, 2019, now Pat. No. 11,317,944, which is a (Continued)

(30) Foreign Application Priority Data

Mar. 14, 2011 (EP) ..................... 11158118

(51) Int. Cl.
A61B 17/34 (2006.01)
A61B 5/00 (2006.01)
(Continued)

(52) U.S. Cl.
CPC .......... A61B 17/3468 (2013.01); A61B 5/686 (2013.01); A61B 17/3415 (2013.01);
(Continued)

(58) Field of Classification Search
CPC ...... A61M 2005/1585; A61M 25/0612; A61M 25/0618; A61M 25/0625; A61B 17/3468;
(Continued)

(56) References Cited

U.S. PATENT DOCUMENTS 5,628,765 A * 5/1997 Morita ............. A61B 5/150312
606/181
5,964,718 A 10/1999 Duchon et al.
(Continued)

FOREIGN PATENT DOCUMENTS

EP 3257533 A1 12/2017
EP 3305349 A1 4/2018
(Continued)

OTHER PUBLICATIONS

International Application No. PCT/EP2012/053722 International Preliminary Report on Patentability issued Sep. 17, 2013.
(Continued)

Primary Examiner — Thomas McEvoy
(74) Attorney, Agent, or Firm — TAFT STETTINIUS HOLLISTER LLP; Ryan O. White; Derek B. Lavender

(57) ABSTRACT

Single use inserter system comprising a housing part and a lid part, the inserter system comprising a carrier part in an initial position in the housing and a drive unit comprising a first drive part attached to the housing, the drive unit comprising at least one spring element supported by the first drive part, wherein the drive unit is configured for moving the carrier part from a first position to a second position in relation to the housing in an insertion direction along a first axis. The inserter system comprises a transcutaneous device having a proximal surface and a distal surface, wherein the transcutaneous device is detachably attached to the carrier part, the inserter system comprising at least one transport protection element preventing movement of the carrier part in a direction along the first axis thereby supporting the carrier part in the initial position.

10 Claims, 7 Drawing Sheets

Related U.S. Application Data continuation of application No. 14/003,193, filed as application No. PCT/EP2012/053722 on Mar. 5, 2012, now Pat. No. 10,194,938.

(60) Provisional application No. 61/452,836, filed on Mar. 15, 2011.

(51) Int. Cl.
*A61M 5/158* (2006.01)
*A61B 17/00* (2006.01)

(52) U.S. Cl.
CPC ..... *A61M 5/158* (2013.01); *A61B 2017/0023* (2013.01); *A61B 2017/00367* (2013.01); *A61B 2017/347* (2013.01); *A61M 2005/1585* (2013.01)

(58) Field of Classification Search
CPC ...... A61B 5/6848; A61B 5/151–15198; A61B 5/150412; A61B 5/150419; A61B 5/150427; A61B 5/150503; A61B 5/1519; A61B 5/15101; A61B 5/150541; A61B 5/150549; A61B 5/150557; A61B 5/150564; A61B 5/150908; A61B 5/150717

See application file for complete search history.

(56) References Cited

U.S. PATENT DOCUMENTS

| | | | |
|---|---|---|---|
| 6,390,990 B1 * | 5/2002 | Marshall .......... | A61B 5/150519 600/573 |
| 10,071,210 B2 | 9/2018 | Gray | |
| 10,292,641 B2 | 5/2019 | Bureau et al. | |
| 10,293,101 B2 | 5/2019 | Brewer et al. | |
| 10,369,274 B2 | 8/2019 | O'Connor et al. | |
| 10,369,289 B2 | 8/2019 | Cabiri et al. | |
| 10,376,638 B2 | 8/2019 | Levesque et al. | |
| 10,413,661 B2 | 9/2019 | Kamen et al. | |
| 10,432,403 B2 | 10/2019 | Moskal | |
| 10,434,245 B2 | 10/2019 | Yodfat et al. | |
| 10,434,247 B2 | 10/2019 | Cole et al. | |
| 10,434,248 B1 | 10/2019 | Penake et al. | |
| 10,434,253 B2 | 10/2019 | DiPerna et al. | |
| 10,434,285 B2 | 10/2019 | Schoonmaker et al. | |
| 10,438,696 B2 | 10/2019 | Shapley et al. | |
| 10,441,356 B2 | 10/2019 | Zarins et al. | |
| 10,441,713 B1 | 10/2019 | Feldman et al. | |
| 10,441,718 B2 | 10/2019 | Tchao et al. | |
| 10,441,723 B2 | 10/2019 | Nazzaro | |
| 10,441,775 B2 | 10/2019 | Schriver et al. | |
| 10,449,290 B2 | 10/2019 | Shapley et al. | |
| 10,449,291 B2 | 10/2019 | Hadian et al. | |
| 10,449,296 B2 | 10/2019 | Kapas et al. | |
| 10,449,306 B2 | 10/2019 | Grover et al. | |
| 10,463,572 B2 | 11/2019 | Shor et al. | |
| 10,463,785 B2 | 11/2019 | Dewey | |
| 10,463,787 B2 | 11/2019 | Shor et al. | |
| 10,463,791 B2 | 11/2019 | Shergold et al. | |
| 10,471,203 B2 | 11/2019 | Chappel et al. | |
| 10,471,206 B2 | 11/2019 | Dittrich | |
| 10,478,550 B2 | 11/2019 | Hadvary et al. | |
| 10,478,552 B2 | 11/2019 | Cronenberg et al. | |
| 10,478,554 B2 | 11/2019 | Bazargan et al. | |
| 10,478,555 B2 | 11/2019 | Radojicic | |
| 10,481,024 B2 | 11/2019 | Wade et al. | |
| 10,483,000 B2 | 11/2019 | Saint et al. | |
| 10,485,923 B2 | 11/2019 | Schiendzielorz | |
| 10,485,926 B2 | 11/2019 | Vanderveen et al. | |
| 10,485,937 B2 | 11/2019 | Yodfat et al. | |
| 10,489,617 B2 | 11/2019 | Salem et al. | |
| 10,493,201 B2 | 12/2019 | Cole et al. | |
| 10,493,202 B2 | 12/2019 | Hayter | |
| 10,493,203 B2 | 12/2019 | Yodfat et al. | |
| 10,500,352 B2 | 12/2019 | Grant et al. | |
| 10,507,316 B2 | 12/2019 | Fielder et al. | |
| 10,512,724 B2 | 12/2019 | Renstad et al. | |
| 10,525,193 B2 | 1/2020 | Schauderna | |
| 10,525,247 B2 | 1/2020 | Bellrichard et al. | |
| 10,532,150 B2 | 1/2020 | Bazargan et al. | |
| 10,532,151 B2 | 1/2020 | Wei | |
| 10,532,155 B2 | 1/2020 | Schiendzielorz | |
| 10,532,159 B2 | 1/2020 | Torsten et al. | |
| 10,532,835 B2 | 1/2020 | Chong et al. | |
| 10,537,681 B2 | 1/2020 | Tan-Malecki et al. | |
| 10,539,481 B2 | 1/2020 | Plahey et al. | |
| 10,542,921 B2 | 1/2020 | Kuhn | |
| 10,542,936 B2 | 1/2020 | Goldberg et al. | |
| 10,549,029 B2 | 2/2020 | Agard et al. | |
| 10,549,033 B2 | 2/2020 | Shimizu | |
| 10,549,034 B2 | 2/2020 | Eggert et al. | |
| 10,549,036 B2 | 2/2020 | Starkweather et al. | |
| 10,549,079 B2 | 2/2020 | Burton et al. | |
| 10,556,059 B2 | 2/2020 | Cross et al. | |
| 10,556,063 B2 | 2/2020 | Murphy, Jr. et al. | |
| 10,561,785 B2 | 2/2020 | Roy et al. | |
| 10,561,788 B2 | 2/2020 | Roy | |
| 10,561,789 B2 | 2/2020 | Mastrototaro et al. | |
| 10,561,826 B2 | 2/2020 | Amano et al. | |
| 10,561,831 B2 | 2/2020 | Kato | |
| 10,569,011 B2 | 2/2020 | Dilanni et al. | |
| 10,569,012 B2 | 2/2020 | Schabbach et al. | |
| 10,569,014 B2 | 2/2020 | Hanson et al. | |
| 10,576,199 B2 | 3/2020 | Sealfon et al. | |
| 10,576,203 B2 | 3/2020 | Amon et al. | |
| 10,576,204 B2 | 3/2020 | Estes et al. | |
| 10,583,241 B2 | 3/2020 | Wu et al. | |
| 10,583,247 B2 | 3/2020 | Mandro | |
| 10,589,023 B2 | 3/2020 | Cindrich et al. | |
| 10,589,028 B2 | 3/2020 | Cabiri et al. | |
| 10,596,317 B2 | 3/2020 | Nakanishi | |
| 10,596,362 B2 | 3/2020 | Fielder et al. | |
| 10,610,638 B2 | 4/2020 | Cabiri et al. | |
| 10,610,639 B2 | 4/2020 | Cabiri et al. | |
| 10,610,644 B2 | 4/2020 | Mazlish et al. | |
| 10,617,817 B2 | 4/2020 | Hwang et al. | |
| 10,617,820 B2 | 4/2020 | O'Connor et al. | |
| 10,625,016 B2 | 4/2020 | Amon et al. | |
| 10,625,017 B2 | 4/2020 | Searle et al. | |
| 10,625,018 B2 | 4/2020 | Destefano et al. | |
| 10,632,248 B2 | 4/2020 | Stefanov et al. | |
| 10,632,249 B2 | 4/2020 | Marbet et al. | |
| 10,632,253 B2 | 4/2020 | Uchiyama et al. | |
| 10,632,256 B2 | 4/2020 | Sasaki | |
| 10,632,257 B2 | 4/2020 | Estes et al. | |
| 10,635,784 B2 | 4/2020 | Rubalcaba, Jr. et al. | |
| 10,639,417 B2 | 5/2020 | Roberts | |
| 10,639,418 B2 | 5/2020 | Kamen et al. | |
| 10,639,661 B2 | 5/2020 | Fontana | |
| 10,646,643 B2 | 5/2020 | Cabiri et al. | |
| 10,646,652 B2 | 5/2020 | McCullough et al. | |
| 10,646,653 B2 | 5/2020 | Despa et al. | |
| 10,653,828 B2 | 5/2020 | Brown et al. | |
| 10,653,829 B2 | 5/2020 | Barchen et al. | |
| 10,653,833 B2 | 5/2020 | Kamen et al. | |
| 10,653,835 B2 | 5/2020 | Dobbles et al. | |
| 10,653,846 B2 | 5/2020 | Weibel et al. | |
| 10,656,894 B2 | 5/2020 | Fryman | |
| 10,661,006 B2 | 5/2020 | Antonio et al. | |
| 10,661,007 B2 | 5/2020 | Estes | |
| 10,661,008 B2 | 5/2020 | Brewer et al. | |
| 10,661,067 B2 | 5/2020 | Kodama | |
| 10,668,209 B2 | 6/2020 | Montalvo et al. | |
| 10,668,210 B2 | 6/2020 | Kamen et al. | |
| 10,668,213 B2 | 6/2020 | Cabiri | |
| 10,668,227 B2 | 6/2020 | Caspers | |
| 10,675,055 B2 | 6/2020 | Chong et al. | |
| 10,675,333 B2 | 6/2020 | Ning et al. | |
| 10,675,404 B2 | 6/2020 | Pizzochero et al. | |
| 10,682,458 B2 | 6/2020 | Wu et al. | |
| 10,682,460 B2 | 6/2020 | Adams et al. | |
| 10,682,461 B2 | 6/2020 | Oakes | |

(56) References Cited

U.S. PATENT DOCUMENTS

| | | |
|---|---|---|
| 10,682,463 B2 | 6/2020 | Kamen et al. |
| 10,685,749 B2 | 6/2020 | Hayter et al. |
| 10,688,241 B2 | 6/2020 | Yang |
| 10,688,243 B2 | 6/2020 | Cabiri |
| 10,688,294 B2 | 6/2020 | Cowan et al. |
| 10,709,834 B2 | 7/2020 | Chiu et al. |
| 10,716,891 B2 | 7/2020 | Saab et al. |
| 10,716,893 B2 | 7/2020 | Gray et al. |
| 10,716,895 B2 | 7/2020 | Brewer et al. |
| 10,716,896 B2 | 7/2020 | O'Connor et al. |
| 10,716,926 B2 | 7/2020 | Burton et al. |
| 10,719,584 B2 | 7/2020 | Drew |
| 10,722,640 B2 | 7/2020 | McLaughlin |
| 10,722,643 B2 | 7/2020 | Gray et al. |
| 10,722,646 B2 | 7/2020 | Cole et al. |
| 10,722,647 B2 | 7/2020 | Gray |
| 10,722,650 B2 | 7/2020 | Duke et al. |
| 10,722,661 B2 | 7/2020 | Mandro et al. |
| 10,729,842 B2 | 8/2020 | Hooven et al. |
| 10,729,844 B2 | 8/2020 | Cole et al. |
| 10,729,849 B2 | 8/2020 | Finan et al. |
| 10,737,015 B2 | 8/2020 | Estes |
| 10,737,016 B2 | 8/2020 | Smith et al. |
| 10,737,021 B2 | 8/2020 | Deck |
| 10,737,022 B2 | 8/2020 | Mou et al. |
| 10,737,024 B2 | 8/2020 | Schmid |
| 10,737,026 B2 | 8/2020 | Teutsch |
| 10,737,038 B2 | 8/2020 | Cole et al. |
| 10,744,257 B2 | 8/2020 | Mandro et al. |
| 10,751,467 B2 | 8/2020 | Kamen et al. |
| 10,751,468 B2 | 8/2020 | Abal |
| 10,751,476 B2 | 8/2020 | Gazeley et al. |
| 10,751,478 B2 | 8/2020 | Nazzaro |
| 10,757,219 B2 | 8/2020 | Moskal |
| 10,758,675 B2 | 9/2020 | Mazlish et al. |
| 10,758,683 B2 | 9/2020 | Gibson et al. |
| 10,758,721 B2 | 9/2020 | Sonderegger et al. |
| 10,765,801 B2 | 9/2020 | McCullough |
| 10,765,803 B2 | 9/2020 | Gonnelli |
| 10,765,807 B2 | 9/2020 | Allis et al. |
| 10,772,796 B2 | 9/2020 | Kavazov |
| 10,773,019 B2 | 9/2020 | Searle et al. |
| 10,780,215 B2 | 9/2020 | Rosinko et al. |
| 10,780,216 B2 | 9/2020 | Farra |
| 10,780,217 B2 | 9/2020 | Nazzaro et al. |
| 10,780,220 B2 | 9/2020 | Gray |
| 10,780,223 B2 | 9/2020 | Desborough et al. |
| 10,792,419 B2 | 10/2020 | Kamen et al. |
| 10,792,424 B2 | 10/2020 | Sasaki |
| 10,792,425 B2 | 10/2020 | Joseph et al. |
| 10,792,440 B2 | 10/2020 | Mandro et al. |
| 10,799,630 B2 | 10/2020 | McCullough |
| 10,799,631 B2 | 10/2020 | Barmaimon et al. |
| 10,799,632 B2 | 10/2020 | Kohlbrecher |
| 10,806,851 B2 | 10/2020 | Rosinko |
| 10,806,854 B2 | 10/2020 | O'Connor et al. |
| 10,806,855 B2 | 10/2020 | Destefano et al. |
| 10,806,859 B2 | 10/2020 | Desborough et al. |
| 10,814,061 B2 | 10/2020 | Bene et al. |
| 10,814,062 B2 | 10/2020 | Gyory |
| 11,135,362 B2 | 10/2021 | DiPerna et al. |
| 11,136,971 B2 | 10/2021 | Kamen et al. |
| 11,136,972 B2 | 10/2021 | Kamen et al. |
| 11,173,244 B2 | 11/2021 | Agard et al. |
| 11,179,514 B2 | 11/2021 | Yodfat et al. |
| 11,241,534 B2 | 2/2022 | Miller et al. |
| 11,261,858 B2 | 3/2022 | Kamen et al. |
| 11,293,425 B2 | 4/2022 | Kamen et al. |
| 11,339,774 B2 | 5/2022 | Gray et al. |
| 11,391,273 B2 | 7/2022 | Kamen et al. |
| 11,406,753 B2 | 8/2022 | Gray et al. |
| 11,408,414 B2 | 8/2022 | Kamen et al. |
| 11,413,391 B2 | 8/2022 | Gray |
| 11,491,273 B2 | 11/2022 | Gray |
| 11,497,846 B2 | 11/2022 | Kamen et al. |
| 11,534,543 B2 | 12/2022 | Kamen et al. |
| 11,690,952 B2 | 7/2023 | Kamen et al. |
| 11,690,953 B2 | 7/2023 | Lawrence et al. |
| 11,712,513 B2 | 8/2023 | Gray et al. |
| 11,712,517 B2 | 8/2023 | Lawrence et al. |
| 11,717,609 B2 | 8/2023 | Kamen et al. |
| 11,738,139 B2 | 8/2023 | Gray |
| 11,786,651 B2 | 10/2023 | Kamen et al. |
| 11,813,427 B2 | 11/2023 | Kamen et al. |
| 11,904,134 B2 | 2/2024 | Gray |
| 11,918,782 B2 | 3/2024 | Jennewine |
| 11,992,650 B2 | 5/2024 | Kamen et al. |
| 2002/0103499 A1 | 8/2002 | Perez et al. |
| 2003/0187394 A1 | 10/2003 | Wilkinson et al. |
| 2004/0127818 A1 | 7/2004 | Roe et al. |
| 2005/0065466 A1 | 3/2005 | Vedrine |
| 2005/0101912 A1 | 5/2005 | Faust et al. |
| 2006/0106346 A1 | 5/2006 | Sullivan et al. |
| 2007/0010841 A1* | 1/2007 | Teo .................. A61B 5/150022 606/181 |
| 2007/0021729 A1 | 1/2007 | Mogensen et al. |
| 2007/0124002 A1 | 5/2007 | Estes et al. |
| 2007/0191770 A1 | 8/2007 | Moberg et al. |
| 2008/0215035 A1 | 9/2008 | Yodfat et al. |
| 2008/0234630 A1 | 9/2008 | Iddan et al. |
| 2009/0218243 A1 | 9/2009 | Gyrn et al. |
| 2009/0326453 A1 | 12/2009 | Adams et al. |
| 2010/0049128 A1 | 2/2010 | McKenzie et al. |
| 2010/0094251 A1 | 4/2010 | Estes |
| 2010/0135831 A1 | 6/2010 | Jacobsen |
| 2010/0145303 A1 | 6/2010 | Yodfat et al. |
| 2010/0168670 A1 | 7/2010 | Srisathapat et al. |
| 2010/0241103 A1 | 9/2010 | Kraft et al. |
| 2011/0028982 A1 | 2/2011 | Lacy |
| 2011/0040247 A1 | 2/2011 | Mandro et al. |
| 2011/0112484 A1 | 5/2011 | Carter et al. |
| 2011/0112696 A1 | 5/2011 | Yodfat et al. |
| 2011/0118578 A1 | 5/2011 | Timmerman |
| 2011/0160652 A1 | 6/2011 | Yodfat et al. |
| 2011/0160666 A1 | 6/2011 | Hanson et al. |
| 2011/0313357 A1 | 12/2011 | Skutnik et al. |
| 2012/0078170 A1 | 3/2012 | Smith et al. |
| 2012/0136300 A1 | 5/2012 | Schoonmaker et al. |
| 2012/0150123 A1 | 6/2012 | Lawrence et al. |
| 2012/0209085 A1 | 8/2012 | Degen et al. |
| 2012/0238851 A1 | 9/2012 | Kamen et al. |
| 2013/0046239 A1 | 2/2013 | Gonnelli et al. |
| 2013/0046508 A1 | 2/2013 | Sur et al. |
| 2013/0053823 A1 | 2/2013 | Fiering et al. |
| 2013/0060233 A1 | 3/2013 | O'Connor et al. |
| 2013/0138075 A1 | 5/2013 | Lambert |
| 2013/0226138 A1 | 8/2013 | Sia |
| 2013/0237955 A1 | 9/2013 | Neta et al. |
| 2014/0025002 A1 | 1/2014 | Qi et al. |
| 2014/0031793 A1 | 1/2014 | Constantineau et al. |
| 2014/0052096 A1 | 2/2014 | Searle et al. |
| 2014/0054883 A1 | 2/2014 | Lanigan et al. |
| 2014/0127048 A1 | 5/2014 | Dilanni et al. |
| 2014/0128815 A1 | 5/2014 | Cabiri et al. |
| 2014/0276379 A1 | 9/2014 | Uram et al. |
| 2014/0276536 A1 | 9/2014 | Estes |
| 2014/0323961 A1 | 10/2014 | Blomquist et al. |
| 2014/0358112 A1 | 12/2014 | Smith et al. |
| 2015/0025503 A1 | 1/2015 | Searle et al. |
| 2015/0073384 A1 | 3/2015 | Limaye |
| 2015/0080799 A1 | 3/2015 | Schneider et al. |
| 2015/0080800 A1 | 3/2015 | Cronenberg |
| 2015/0105720 A1 | 4/2015 | Montalvo et al. |
| 2015/0112269 A1 | 4/2015 | Sumida et al. |
| 2015/0209505 A1 | 7/2015 | Hanson et al. |
| 2015/0273201 A1 | 10/2015 | Tallarida et al. |
| 2015/0314117 A1 | 11/2015 | Arami et al. |
| 2016/0051750 A1 | 2/2016 | Tsoukalis |
| 2016/0074578 A1 | 3/2016 | Xu et al. |
| 2016/0082182 A1 | 3/2016 | Gregory et al. |
| 2016/0089056 A1 | 3/2016 | Limaye et al. |
| 2016/0089524 A1 | 3/2016 | Anderson |
| 2016/0144105 A1 | 5/2016 | Hooven et al. |
| 2016/0193407 A1 | 7/2016 | Qin et al. |

(56) References Cited

U.S. PATENT DOCUMENTS

| | | |
|---|---|---|
| 2016/0346469 A1 | 12/2016 | Shubinsky et al. |
| 2017/0080157 A1 | 3/2017 | Cabiri et al. |
| 2017/0100542 A1 | 4/2017 | Norton et al. |
| 2017/0232191 A1 | 8/2017 | Smith et al. |
| 2017/0258987 A1 | 9/2017 | Caspers |
| 2017/0290971 A1 | 10/2017 | Hedmann et al. |
| 2017/0296741 A1 | 10/2017 | Gregory |
| 2017/0296742 A1 | 10/2017 | Stefanov |
| 2017/0340827 A1 | 11/2017 | Nazzaro et al. |
| 2017/0340841 A1 | 11/2017 | Sasaki |
| 2017/0351841 A1 | 12/2017 | Moskal |
| 2017/0351851 A1 | 12/2017 | Wang et al. |
| 2017/0368260 A1 | 12/2017 | McCullough et al. |
| 2018/0008768 A1 | 1/2018 | Prescher et al. |
| 2018/0028744 A1 | 2/2018 | Kim |
| 2018/0036476 A1 | 2/2018 | McCullough et al. |
| 2018/0071450 A1 | 3/2018 | Ruhland |
| 2018/0110420 A1 | 4/2018 | Pekander |
| 2018/0185573 A1 | 7/2018 | Niklaus |
| 2018/0193563 A1 | 7/2018 | Krasnow et al. |
| 2018/0200434 A1 | 7/2018 | Mazlish et al. |
| 2018/0200440 A1 | 7/2018 | Mazlish et al. |
| 2018/0207360 A1 | 7/2018 | Juretich et al. |
| 2018/0214635 A1 | 8/2018 | Raman et al. |
| 2018/0221571 A1 | 8/2018 | Carbone et al. |
| 2018/0228967 A1 | 8/2018 | Hopkins et al. |
| 2018/0271455 A1 | 9/2018 | Zhong et al. |
| 2018/0280607 A1 | 10/2018 | Richards et al. |
| 2018/0280608 A1 | 10/2018 | Gillett et al. |
| 2018/0280619 A1 | 10/2018 | Finan et al. |
| 2018/0291882 A1 | 10/2018 | Algawi et al. |
| 2018/0296757 A1 | 10/2018 | Finan et al. |
| 2018/0344926 A1 | 12/2018 | Brandenburg et al. |
| 2018/0361061 A1 | 12/2018 | Andretta |
| 2018/0372085 A1 | 12/2018 | Veischow et al. |
| 2019/0009019 A1 | 1/2019 | Shor et al. |
| 2019/0009022 A1 | 1/2019 | Oakes |
| 2019/0009023 A1 | 1/2019 | Diperna et al. |
| 2019/0015585 A1 | 1/2019 | Smith |
| 2019/0022317 A1 | 1/2019 | Uddin et al. |
| 2019/0060562 A1 | 2/2019 | Olivas et al. |
| 2019/0083057 A1 | 3/2019 | Saul et al. |
| 2019/0083702 A1 | 3/2019 | Nekouzadeh et al. |
| 2019/0091404 A1 | 3/2019 | Nazzaro et al. |
| 2019/0091417 A1 | 3/2019 | McCaffrey et al. |
| 2019/0111202 A1 | 4/2019 | Falkovich |
| 2019/0117896 A1 | 4/2019 | Booth et al. |
| 2019/0117897 A1 | 4/2019 | Avery et al. |
| 2019/0125226 A1 | 5/2019 | Koya et al. |
| 2019/0175828 A1 | 6/2019 | List et al. |
| 2019/0262535 A1 | 8/2019 | Shubinsky et al. |
| 2019/0275243 A1 | 9/2019 | Deck et al. |
| 2019/0275249 A1 | 9/2019 | von Campenhausen |
| 2019/0282751 A1 | 9/2019 | Della Bidia |
| 2019/0290845 A1 | 9/2019 | List |
| 2019/0298485 A1 | 10/2019 | Forsell |
| 2019/0298912 A1 | 10/2019 | Spencer et al. |
| 2019/0298914 A1 | 10/2019 | Kamen et al. |
| 2019/0298916 A1 | 10/2019 | List |
| 2019/0298918 A1 | 10/2019 | Jallon |
| 2019/0298921 A1 | 10/2019 | Stafford |
| 2019/0298925 A1 | 10/2019 | Cowe et al. |
| 2019/0307943 A1 | 10/2019 | Franano et al. |
| 2019/0307952 A1 | 10/2019 | Butler et al. |
| 2019/0307954 A1 | 10/2019 | Klemm et al. |
| 2019/0307955 A1 | 10/2019 | Levesque et al. |
| 2019/0307970 A1 | 10/2019 | Karen et al. |
| 2019/0314572 A1 | 10/2019 | Yang |
| 2019/0321260 A1 | 10/2019 | Grant et al. |
| 2019/0321544 A1 | 10/2019 | List |
| 2019/0321545 A1 | 10/2019 | Saint |
| 2019/0321546 A1 | 10/2019 | Michaud et al. |
| 2019/0321548 A1 | 10/2019 | Cowan |
| 2019/0321552 A1 | 10/2019 | DiPema et al. |
| 2019/0328963 A1 | 10/2019 | Wolff et al. |
| 2019/0336078 A1 | 11/2019 | Dang et al. |
| 2019/0336678 A1 | 11/2019 | Rule |
| 2019/0336679 A1 | 11/2019 | Staub et al. |
| 2019/0336681 A1 | 11/2019 | Kamen et al. |
| 2019/0336683 A1 | 11/2019 | O'Connor et al. |
| 2019/0341149 A1 | 11/2019 | Chiu et al. |
| 2019/0343434 A1 | 11/2019 | Varsavsky et al. |
| 2019/0344009 A1 | 11/2019 | Damiano et al. |
| 2019/0344010 A1 | 11/2019 | Pizzochero et al. |
| 2019/0344057 A1 | 11/2019 | Cima et al. |
| 2019/0350501 A1 | 11/2019 | Blomquist et al. |
| 2019/0351131 A1 | 11/2019 | Butterfield et al. |
| 2019/0351132 A1 | 11/2019 | Pippin et al. |
| 2019/0351133 A1 | 11/2019 | Grant, Jr. et al. |
| 2019/0351134 A1 | 11/2019 | Cook et al. |
| 2019/0351135 A1 | 11/2019 | Naftalovitz et al. |
| 2019/0351138 A1 | 11/2019 | Bhandar et al. |
| 2019/0351143 A1 | 11/2019 | Egloff et al. |
| 2019/0351209 A1 | 11/2019 | Butziger et al. |
| 2019/0358393 A1 | 11/2019 | Marbet |
| 2019/0358395 A1 | 11/2019 | Olson et al. |
| 2019/0358437 A1 | 11/2019 | Schwartz et al. |
| 2019/0365282 A1 | 12/2019 | Gibson |
| 2019/0365985 A1 | 12/2019 | Zidon et al. |
| 2019/0365986 A1 | 12/2019 | Coiner et al. |
| 2019/0365987 A1 | 12/2019 | Gibson et al. |
| 2019/0365993 A1 | 12/2019 | Staub et al. |
| 2019/0366002 A1 | 12/2019 | Verlaak et al. |
| 2019/0366011 A1 | 12/2019 | Ring |
| 2019/0366012 A1 | 12/2019 | Gross et al. |
| 2019/0368484 A1 | 12/2019 | Chappel et al. |
| 2019/0374434 A1 | 12/2019 | Kamdar et al. |
| 2019/0374706 A1 | 12/2019 | Cabiri et al. |
| 2019/0374707 A1 | 12/2019 | Damestani et al. |
| 2019/0374708 A1 | 12/2019 | Cardinali et al. |
| 2019/0374709 A1 | 12/2019 | Cole et al. |
| 2019/0374711 A1 | 12/2019 | Deliwala |
| 2019/0374714 A1 | 12/2019 | Rioux et al. |
| 2019/0374719 A1 | 12/2019 | Cabiri et al. |
| 2019/0374757 A1 | 12/2019 | Verhoeven et al. |
| 2019/0381238 A1 | 12/2019 | Stonecipher et al. |
| 2019/0381239 A1 | 12/2019 | Cabiri et al. |
| 2019/0381241 A1 | 12/2019 | Bryant et al. |
| 2019/0388609 A1 | 12/2019 | Lanigan et al. |
| 2019/0388612 A1 | 12/2019 | Schramm |
| 2019/0388614 A1 | 12/2019 | Gyrn et al. |
| 2019/0388615 A1 | 12/2019 | Sonderegger et al. |
| 2019/0392938 A1 | 12/2019 | Mermet |
| 2020/0001004 A1 | 1/2020 | Kondo |
| 2020/0001005 A1 | 1/2020 | Politis et al. |
| 2020/0001006 A1 | 1/2020 | Pizzochero et al. |
| 2020/0001007 A1 | 1/2020 | Miesel et al. |
| 2020/0009315 A1 | 1/2020 | Brouet et al. |
| 2020/0009317 A1 | 1/2020 | Cronenberg et al. |
| 2020/0009318 A1 | 1/2020 | Kamen et al. |
| 2020/0009319 A1 | 1/2020 | Ludolph |
| 2020/0009324 A1 | 1/2020 | Barrows et al. |
| 2020/0009331 A1 | 1/2020 | Kamen et al. |
| 2020/0016328 A1 | 1/2020 | Cane' et al. |
| 2020/0016329 A1 | 1/2020 | Schabbach et al. |
| 2020/0016330 A1 | 1/2020 | Kapas et al. |
| 2020/0016333 A1 | 1/2020 | Soares et al. |
| 2020/0016335 A1 | 1/2020 | DiPerna et al. |
| 2020/0016336 A1 | 1/2020 | Patek et al. |
| 2020/0023119 A1 | 1/2020 | Barnes et al. |
| 2020/0023121 A1 | 1/2020 | Thomas et al. |
| 2020/0023122 A1 | 1/2020 | McCullough et al. |
| 2020/0023123 A1 | 1/2020 | O'Connor et al. |
| 2020/0023129 A1 | 1/2020 | Day et al. |
| 2020/0025184 A1 | 1/2020 | Gyory |
| 2020/0027541 A1 | 1/2020 | Xavier et al. |
| 2020/0028914 A1 | 1/2020 | Xavier et al. |
| 2020/0030528 A1 | 1/2020 | Burke et al. |
| 2020/0030529 A1 | 1/2020 | DiPerna et al. |
| 2020/0030530 A1 | 1/2020 | Huang et al. |
| 2020/0030531 A1 | 1/2020 | Day et al. |
| 2020/0030532 A1 | 1/2020 | Day et al. |
| 2020/0030533 A1 | 1/2020 | Day et al. |
| 2020/0030590 A1 | 1/2020 | Buchman et al. |

(56) References Cited

U.S. PATENT DOCUMENTS

| | | |
|---|---|---|
| 2020/0030592 A1 | 1/2020 | Cheche |
| 2020/0035355 A1 | 1/2020 | Xavier et al. |
| 2020/0038588 A1 | 2/2020 | Varsavsky et al. |
| 2020/0043588 A1 | 2/2020 | Mougiakakou et al. |
| 2020/0046904 A1 | 2/2020 | Schader et al. |
| 2020/0054822 A1 | 2/2020 | Dewey |
| 2020/0054825 A1 | 2/2020 | Kamen et al. |
| 2020/0054826 A1 | 2/2020 | Diianni et al. |
| 2020/0054832 A1 | 2/2020 | Jeong et al. |
| 2020/0061285 A1 | 2/2020 | Reeves |
| 2020/0061287 A1 | 2/2020 | Chappel et al. |
| 2020/0069865 A1 | 3/2020 | Day et al. |
| 2020/0069869 A1 | 3/2020 | Grant et al. |
| 2020/0069871 A1 | 3/2020 | Yavorsky et al. |
| 2020/0069873 A1 | 3/2020 | Pizzochero et al. |
| 2020/0069875 A1 | 3/2020 | Nazzaro et al. |
| 2020/0077340 A1 | 3/2020 | Kruse |
| 2020/0077948 A1 | 3/2020 | Schmid |
| 2020/0078511 A1 | 3/2020 | Focht et al. |
| 2020/0078513 A1 | 3/2020 | Wei |
| 2020/0086041 A1 | 3/2020 | Fuchs et al. |
| 2020/0086042 A1 | 3/2020 | Kamen et al. |
| 2020/0086043 A1 | 3/2020 | Saint |
| 2020/0086044 A1 | 3/2020 | Streit et al. |
| 2020/0086045 A1 | 3/2020 | Azapagic et al. |
| 2020/0086051 A1 | 3/2020 | Grygus et al. |
| 2020/0093980 A1 | 3/2020 | McDermott et al. |
| 2020/0093984 A1 | 3/2020 | Shor et al. |
| 2020/0098463 A1 | 3/2020 | Arunachalam et al. |
| 2020/0098464 A1 | 3/2020 | Velado et al. |
| 2020/0101218 A1 | 4/2020 | Shapley et al. |
| 2020/0101219 A1 | 4/2020 | Wang et al. |
| 2020/0101222 A1 | 4/2020 | Lintereur et al. |
| 2020/0101223 A1 | 4/2020 | Lintereur et al. |
| 2020/0101224 A1 | 4/2020 | Lintereur et al. |
| 2020/0101225 A1 | 4/2020 | O'Connor et al. |
| 2020/0101226 A1 | 4/2020 | Rosinko et al. |
| 2020/0108201 A1 | 4/2020 | Ben-David et al. |
| 2020/0108204 A1 | 4/2020 | Mazlish et al. |
| 2020/0111556 A1 | 4/2020 | Schmidlin et al. |
| 2020/0113515 A1 | 4/2020 | O'Connor et al. |
| 2020/0114064 A1 | 4/2020 | Reeves |
| 2020/0114068 A1 | 4/2020 | Schmidlin et al. |
| 2020/0114069 A1 | 4/2020 | Searle et al. |
| 2020/0114072 A1 | 4/2020 | Addiego et al. |
| 2020/0114075 A1 | 4/2020 | Morrow et al. |
| 2020/0114076 A1 | 4/2020 | Ulrich et al. |
| 2020/0114080 A1 | 4/2020 | Barmaimon et al. |
| 2020/0118676 A1 | 4/2020 | Spohn et al. |
| 2020/0121848 A1 | 4/2020 | Schmidlin et al. |
| 2020/0121849 A1 | 4/2020 | Christenson et al. |
| 2020/0121850 A1 | 4/2020 | Christenson et al. |
| 2020/0121854 A1 | 4/2020 | Norton et al. |
| 2020/0121937 A1 | 4/2020 | Yoder et al. |
| 2020/0129692 A1 | 4/2020 | Kim et al. |
| 2020/0135323 A1 | 4/2020 | Bazargan |
| 2020/0138852 A1 | 5/2020 | Chattaraj et al. |
| 2020/0138911 A1 | 5/2020 | Joseph et al. |
| 2020/0139137 A1 | 5/2020 | Crawford |
| 2020/0146938 A1 | 5/2020 | Bourelle et al. |
| 2020/0147298 A1 | 5/2020 | Traverso et al. |
| 2020/0147303 A1 | 5/2020 | Lee |
| 2020/0147304 A1 | 5/2020 | Crouther et al. |
| 2020/0147305 A1 | 5/2020 | Estes |
| 2020/0147309 A1 | 5/2020 | Quinn et al. |
| 2020/0155755 A1 | 5/2020 | Chaves et al. |
| 2020/0155757 A1 | 5/2020 | Gregory et al. |
| 2020/0155758 A1 | 5/2020 | Reeves |
| 2020/0164142 A1 | 5/2020 | Poetschke |
| 2020/0164143 A1 | 5/2020 | Cardinali et al. |
| 2020/0164159 A1 | 5/2020 | Chattaraj et al. |
| 2020/0164199 A1 | 5/2020 | Gerlach et al. |
| 2020/0168316 A1 | 5/2020 | Kamen |
| 2020/0171236 A1 | 6/2020 | McCullough et al. |
| 2020/0171294 A1 | 6/2020 | Turner et al. |
| 2020/0179592 A1 | 6/2020 | Adams et al. |
| 2020/0179594 A1 | 6/2020 | Yodfat et al. |
| 2020/0179595 A1 | 6/2020 | McDermott et al. |
| 2020/0179596 A1 | 6/2020 | Dechelette et al. |
| 2020/0179598 A1 | 6/2020 | Penake et al. |
| 2020/0179602 A1 | 6/2020 | Mazlish |
| 2020/0179603 A1 | 6/2020 | Rosinko |
| 2020/0179604 A1 | 6/2020 | Friedli |
| 2020/0179610 A1 | 6/2020 | Bar-El et al. |
| 2020/0188578 A1 | 6/2020 | Bar-El et al. |
| 2020/0188580 A1 | 6/2020 | Gregory et al. |
| 2020/0188581 A1 | 6/2020 | Diianni et al. |
| 2020/0188585 A1 | 6/2020 | Petisce et al. |
| 2020/0188587 A1 | 6/2020 | Sluggett et al. |
| 2020/0188588 A1 | 6/2020 | Estes |
| 2020/0188608 A1 | 6/2020 | Yigal et al. |
| 2020/0197600 A1 | 6/2020 | Chow et al. |
| 2020/0197603 A1 | 6/2020 | Cowe et al. |
| 2020/0197604 A1 | 6/2020 | Fried |
| 2020/0197621 A1 | 6/2020 | Quinn et al. |
| 2020/0197628 A1 | 6/2020 | McCullough et al. |
| 2020/0206417 A1 | 7/2020 | Yodfat et al. |
| 2020/0206418 A1 | 7/2020 | Gonnelli et al. |
| 2020/0206422 A1 | 7/2020 | Cassim |
| 2020/0206429 A1 | 7/2020 | Hering et al. |
| 2020/0214625 A1 | 7/2020 | Hooven et al. |
| 2020/0215264 A1 | 7/2020 | Searle et al. |
| 2020/0215273 A1 | 7/2020 | Gibson et al. |
| 2020/0222624 A1 | 7/2020 | Destefano et al. |
| 2020/0222625 A1 | 7/2020 | Cabiri et al. |
| 2020/0230313 A1 | 7/2020 | Mojarrad et al. |
| 2020/0230314 A1 | 7/2020 | Kondo et al. |
| 2020/0238003 A1 | 7/2020 | Yigal et al. |
| 2020/0238004 A1 | 7/2020 | McCullough |
| 2020/0238006 A1 | 7/2020 | Groszmann et al. |
| 2020/0238012 A1 | 7/2020 | Bar-El et al. |
| 2020/0246538 A1 | 8/2020 | Bar-El et al. |
| 2020/0246541 A1 | 8/2020 | Neftel et al. |
| 2020/0253632 A1 | 8/2020 | Chong et al. |
| 2020/0254172 A1 | 8/2020 | Forster et al. |
| 2020/0254174 A1 | 8/2020 | Kruse et al. |
| 2020/0254176 A1 | 8/2020 | Rytz et al. |
| 2020/0261002 A1 | 8/2020 | Pace |
| 2020/0261642 A1 | 8/2020 | Ben-David et al. |
| 2020/0261643 A1 | 8/2020 | Boyaval et al. |
| 2020/0261645 A1 | 8/2020 | Kamen et al. |
| 2020/0261658 A1 | 8/2020 | Farris et al. |
| 2020/0268962 A1 | 8/2020 | Gamelin |
| 2020/0268975 A1 | 8/2020 | Kim et al. |
| 2020/0272310 A1 | 8/2020 | Vik et al. |
| 2020/0276384 A1 | 9/2020 | Cabiri et al. |
| 2020/0276386 A1 | 9/2020 | Karen et al. |
| 2020/0282131 A1 | 9/2020 | Nazzaro |
| 2020/0289743 A1 | 9/2020 | Chiu et al. |
| 2020/0289745 A1 | 9/2020 | Harris et al. |
| 2020/0297920 A1 | 9/2020 | McLaughlin |
| 2020/0297923 A1 | 9/2020 | Montalvo et al. |
| 2020/0297927 A1 | 9/2020 | Conrath et al. |
| 2020/0306444 A1 | 10/2020 | Politis et al. |
| 2020/0306446 A1 | 10/2020 | Kamen et al. |
| 2020/0306448 A1 | 10/2020 | Schmid |
| 2020/0316290 A1 | 10/2020 | Bourelle et al. |
| 2020/0316291 A1 | 10/2020 | Gibson et al. |
| 2020/0316314 A1 | 10/2020 | Buri et al. |
| 2020/0321094 A1 | 10/2020 | Saint et al. |
| 2020/0324048 A1 | 10/2020 | O'Connor et al. |
| 2020/0324101 A1 | 10/2020 | Hartmann et al. |
| 2020/0330679 A1 | 10/2020 | Cronenberg et al. |
| 2020/0330680 A1 | 10/2020 | Deck |
| 2020/0330701 A1 | 10/2020 | Cole et al. |
| 2020/0335194 A1 | 10/2020 | Jacobson et al. |
| 2020/0338257 A1 | 10/2020 | Hooven et al. |
| 2020/0338262 A1 | 10/2020 | Kamen et al. |
| 2020/0338264 A1 | 10/2020 | Allis et al. |
| 2020/0338266 A1 | 10/2020 | Estes |
| 2021/0060241 A1 | 3/2021 | Kamen et al. |
| 2021/0178074 A1 | 6/2021 | Anderson et al. |
| 2021/0180583 A1 | 6/2021 | Gray |
| 2021/0180584 A1 | 6/2021 | Kamen et al. |

(56) References Cited

U.S. PATENT DOCUMENTS

| | | |
|---|---|---|
| 2021/0190063 A1 | 6/2021 | Gray |
| 2021/0268174 A1 | 9/2021 | Estes et al. |
| 2021/0270255 A1 | 9/2021 | Gray |
| 2021/0293232 A1 | 9/2021 | Kamen et al. |
| 2021/0321914 A1 | 10/2021 | Brister et al. |
| 2021/0330878 A9 | 10/2021 | Margairaz et al. |
| 2021/0330885 A1 | 10/2021 | Halac et al. |
| 2021/0396221 A1 | 12/2021 | Kamen et al. |
| 2022/0001106 A1 | 1/2022 | DiPerna et al. |
| 2022/0023544 A1 | 1/2022 | Anderson et al. |
| 2022/0105261 A1 | 4/2022 | Yodfat et al. |
| 2022/0184303 A1 | 6/2022 | DiPerna et al. |
| 2022/0249769 A1 | 8/2022 | Kamen et al. |
| 2022/0275796 A9 | 9/2022 | Kamen et al. |
| 2022/0280715 A1 | 9/2022 | Gray et al. |
| 2023/0226271 A1 | 7/2023 | Lanigan et al. |
| 2023/0226273 A1 | 7/2023 | Kamen et al. |
| 2023/0226274 A1 | 7/2023 | Kamen et al. |
| 2023/0372606 A1 | 11/2023 | Kamen et al. |
| 2024/0033429 A1 | 2/2024 | Jennewine |
| 2024/0066214 A1 | 2/2024 | Kamen et al. |

FOREIGN PATENT DOCUMENTS

| | | |
|---|---|---|
| EP | 2995330 B1 | 12/2021 |
| EP | 3650370 B1 | 12/2021 |
| EP | 3760253 B1 | 4/2022 |
| EP | 3998095 A1 | 5/2022 |
| EP | 2611478 B1 | 8/2022 |
| EP | 3470100 B1 | 8/2022 |
| EP | 2575935 B2 | 8/2023 |
| EP | 3998095 B1 | 1/2024 |
| EP | 3656699 B1 | 6/2024 |
| EP | 4385551 A2 | 6/2024 |
| WO | 2009010399 A1 | 1/2009 |
| WO | 2010051079 A2 | 5/2010 |
| WO | 2010084268 A1 | 7/2010 |
| WO | 2012123274 A1 | 9/2012 |
| WO | 2015094945 A1 | 6/2015 |
| WO | 2018129519 A1 | 7/2018 |
| WO | 2018210972 A1 | 11/2018 |
| WO | 2018215465 A1 | 11/2018 |
| WO | 2018218082 A1 | 11/2018 |
| WO | 2018222521 A1 | 12/2018 |
| WO | 2018232171 A1 | 12/2018 |
| WO | 2019018838 A1 | 1/2019 |
| WO | 2019022950 A1 | 1/2019 |
| WO | 2019022951 A1 | 1/2019 |
| WO | 2019038751 A1 | 2/2019 |
| WO | 2019043702 A1 | 3/2019 |
| WO | 2019067386 A1 | 4/2019 |
| WO | 2019070472 A1 | 4/2019 |
| WO | 2019074579 A1 | 4/2019 |
| WO | 2019079868 A1 | 5/2019 |
| WO | 2019081947 A1 | 5/2019 |
| WO | 2019186375 A1 | 10/2019 |
| WO | 2019191222 A1 | 10/2019 |
| WO | 2019193089 A1 | 10/2019 |
| WO | 2019197360 A1 | 10/2019 |
| WO | 2019197361 A1 | 10/2019 |
| WO | 2019200198 A1 | 10/2019 |
| WO | 2019213218 A1 | 11/2019 |
| WO | 2019228895 A1 | 12/2019 |
| WO | 2019229686 A1 | 12/2019 |
| WO | 2020005107 A1 | 1/2020 |
| WO | 2020008017 A1 | 1/2020 |
| WO | 2020011572 A1 | 1/2020 |
| WO | 2020012132 A1 | 1/2020 |
| WO | 2020012308 A1 | 1/2020 |
| WO | 2020013691 A1 | 1/2020 |
| WO | 2020016172 A1 | 1/2020 |
| WO | 2020025484 A1 | 2/2020 |
| WO | 2020028009 A1 | 2/2020 |
| WO | 2020043459 A1 | 3/2020 |
| WO | 2020046889 A1 | 3/2020 |
| WO | 2020052723 A1 | 3/2020 |
| WO | 2020055785 A1 | 3/2020 |
| WO | 2020068623 A1 | 4/2020 |
| WO | 2020069926 A1 | 4/2020 |
| WO | 2020072233 A1 | 4/2020 |
| WO | 2020072234 A1 | 4/2020 |
| WO | 2020072235 A1 | 4/2020 |
| WO | 2020074988 A1 | 4/2020 |
| WO | 2020075042 A1 | 4/2020 |
| WO | 2020104872 A1 | 5/2020 |
| WO | 2020109409 A1 | 6/2020 |
| WO | 2020109417 A1 | 6/2020 |
| WO | 2020112515 A1 | 6/2020 |
| WO | 2020118165 A1 | 6/2020 |
| WO | 2020120511 A1 | 6/2020 |
| WO | 2020127181 A1 | 6/2020 |
| WO | 2020141412 A1 | 7/2020 |
| WO | 2020144270 A1 | 7/2020 |
| WO | 2020146306 A1 | 7/2020 |
| WO | 2020148581 A1 | 7/2020 |

OTHER PUBLICATIONS

International Application No. PCT/EP2012/053722 International Search Report completed Mar. 29, 2012.
International Application No. PCT/EP2012/053722 Written Opinion completed Mar. 29, 2012.
U.S. Appl. No. 14/003,193 Office Action dated Apr. 22, 2016.
U.S. Appl. No. 14/003,193 Office Action dated Jun. 1, 2017.
U.S. Appl. No. 14/003,193 Office Action dated May 18, 2018.
U.S. Appl. No. 14/003,193 Office Action dated Oct. 5, 2017.
U.S. Appl. No. 14/003,193 Office Action dated Sep. 13, 2016.
U.S. Appl. No. 14/003,193 Notice of Allowance dated Sep. 25, 2018.

* cited by examiner

INSERTER SYSTEM WITH TRANSPORT PROTECTION

CROSS-REFERENCE

This application is a continuation of U.S. patent application Ser. No. 16/265,832, filed Feb. 1, 2019, which is a continuation application of U.S. patent application Ser. No. 14/003,193, filed Nov. 12, 2013, which is a U.S. National Phase of International Application No. PCT/EP2012/053722, filed Mar. 5, 2012, which claims the benefit of U.S. Provisional Application No. 61/452,836, filed Mar. 15, 2011 and EP application Ser. No. 11/158,118.7, filed Mar. 14, 2011, each of which applications is incorporated herein by reference in its entirety and to which applications we claim priority.

BACKGROUND OF THE INVENTION

The present invention relates to an inserter system, in particular a single use inserter system for placing a transcutaneous device on or near the skin of a patient.

Inserter devices that require manual loading of a drive prior to insertion through the skin of a patient typically have a carrier part carrying the transcutaneous device, wherein the carrier part is in an initial position prior to use, i.e. during storage and transportation, wherein the drive is unbiased/unloaded or substantially unbiased. During transportation, the inserter device may be subject to shock or bumps, which may lead to movement of the unbiased carrier part possibly causing breakage of the packaging, e.g. separation of a seal or cover sheet from the housing. Further, shocks or bumps affecting the inserter system may result in displacement of the transcutaneous device in relation to the carrier part. Displacement of the transcutaneous device may lead to discomfort during insertion or even malfunction of the inserter system.

Typically, preloading of inserter devices with spring elements made of a plastic material, such as POM, is not suitable due to the material properties of the spring element material. Accordingly for inserter devices with plastic spring elements, the drive unit is typically unloaded or substantially unloaded in the initial or transport position, thus requiring loading of a drive unit of the inserter device prior to placing or inserting a transcutaneous part of the inserter device.

SUMMARY

There is a need for inserter systems with capability of withstanding shocks and bumps, e.g. during transportation or relocation.

Accordingly, an inserter system is provided, the inserter system being a single use inserter system comprising a housing part and a lid part, the inserter system comprising a carrier part in an initial position in the housing and a drive unit comprising a first drive part attached to the housing, the drive unit comprising at least one spring element supported by the first drive part, wherein the drive unit is configured for moving the carrier part from a first position to a second position in relation to the housing in an insertion direction along a first axis. The inserter system may comprise a transcutaneous device having a proximal surface and a distal surface, wherein the transcutaneous device is detachably attached to the carrier part, and the inserter system may comprise at least one transport protection element preventing movement of the carrier part in a direction along the first axis thereby supporting the carrier part in the initial position.

The inserter system provides an improved inserter system with increased strength and which is able to withstand shocks and bumps typically experienced during transport and storage without damaging the inserter system.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

The figures are schematic and simplified for clarity, and they merely show details which are essential to the understanding of the invention, while other details have been left out. Throughout, the same reference numerals are used for identical or corresponding parts.

DETAILED DESCRIPTION OF THE INVENTION

Figure 1:
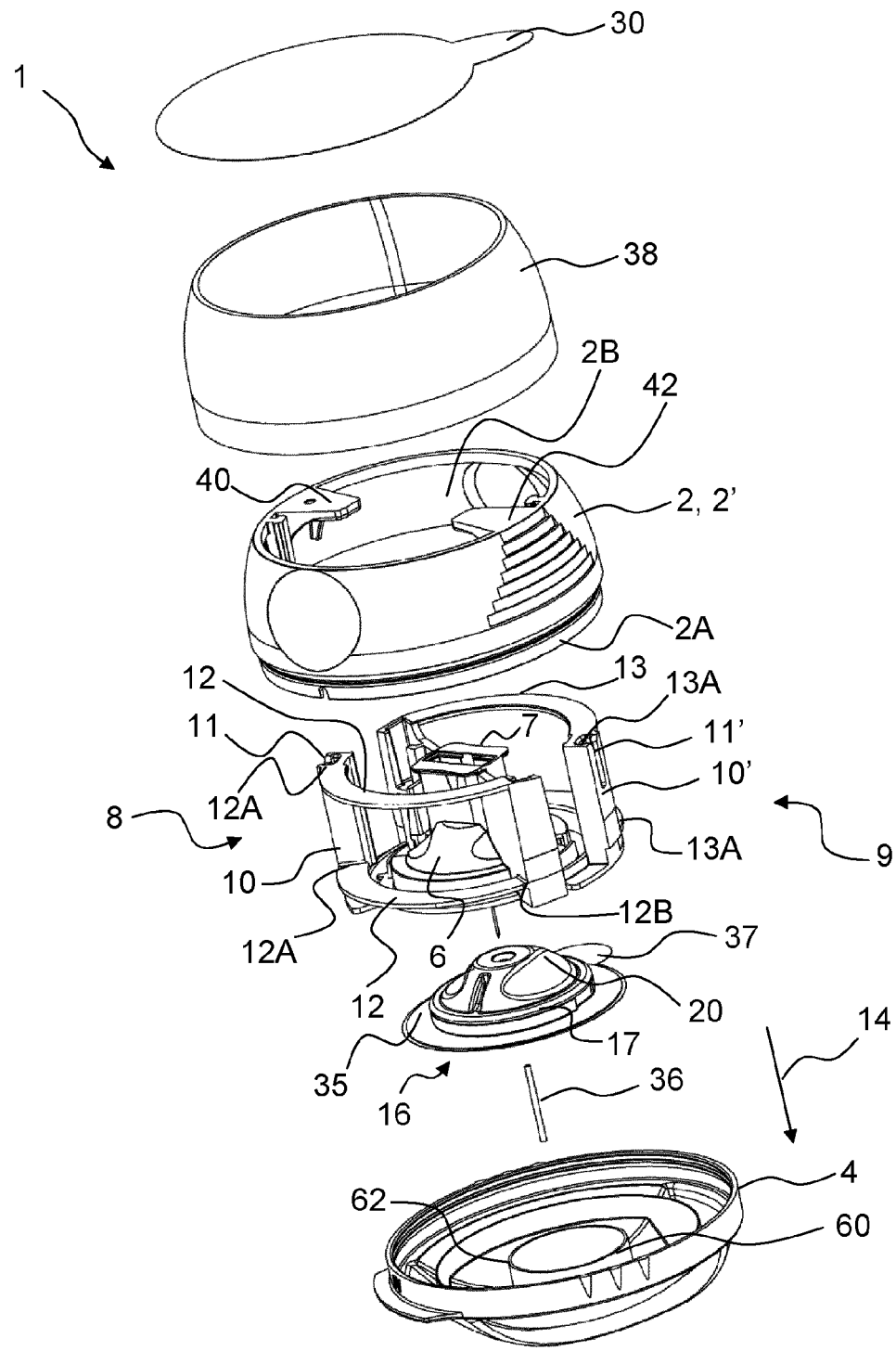
FIG. 1 is an exploded view of an exemplary inserter system.

The inserter system of the present invention alleviates the problems experienced with inserter devices with unbiased drive units.

The inserter system comprises a housing part and optionally a lid part. The housing part has a sidewall with a first end and a second end. A first opening and/or a second opening may be provided at the first end and second end, respectively. When assembled, the lid part may cover the first opening at the first end.

The inserter system may comprise a gas permeable seal or cover sheet. The seal may cover the second opening at the second end of the housing part. The housing part, the seal, and optionally the lid part may define a closed cavity accommodating the transcutaneous device in a sterile environment prior to use. The gas permeable seal allows sterilization of the inserter system upon assembly.

The inserter system comprises a transcutaneous device comprising a base with a distal surface and a proximal surface, the transcutaneous device comprising a transcutaneous element, such as a cannula and/or a sensor element, mounted to the base extending from the proximal surface facing the skin of a patient. The proximal surface may be an adhesive surface for securing the transcutaneous device to a base plate and/or on the skin of the patient. A mounting pad with an adhesive surface may be attached to the proximal surface of the base of the transcutaneous device. The inserter system may comprise a protective layer covering the adhesive surface. The transcutaneous device may comprise locking elements for locking engagement with a base plate.

Prior to use, the carrier part is in an initial position. Prior to inserting the transcutaneous device, a user has to load the inserter system. During loading of the inserter system, the carrier part and the transcutaneous device are moved by the user from the initial position to a first position also referred to as a loaded position or retracted position, e.g. in a retraction direction opposite the insertion direction. By moving the carrier part, e.g. along the first axis and/or around the first axis, to the first position, the drive unit connected to or supporting on the carrier part is biased or loaded for moving the carrier part and the transcutaneous device from the first position to a second position also referred to as an injection position. In the first position, the carrier part is releasably locked by one or more first locking elements, such as a first primary locking element and/or a first secondary locking element on the carrier part. In the first position, the first locking elements may support on a stationary part of the inserter system including the housing part and/or the first drive part. After loading, the inserter system is positioned on the skin and the carrier part is released. Upon release of the first locking element(s), the loaded drive unit moves the carrier part and the transcutaneous device in the insertion direction to the second position placing the transcutaneous element under the skin. After insertion, the carrier part and housing part are removed and the transcutaneous element, optionally including tubing, is ready for use.

The carrier part of the inserter system may comprise a needle hub with a hub base and optionally an insertion needle secured to the hub base, wherein the transcutaneous device is detachably attached to the needle hub. The carrier part may comprise a carrier base, wherein the needle hub is releasably attached to the carrier base. The inserter device may be configured for releasing the needle hub from the carrier base, e.g. in the second position. The inserter device may be configured for moving the needle hub to a third position in the extraction direction upon release from the carrier base in the second position.

The carrier part, with or without an insertion needle, and the drive unit may be molded in a single first unit reducing assembly costs.

The inserter system comprises a stationary part. The stationary part is the parts of the inserter system that are stationary in relation to the skin of a patient when the transcutaneous device is inserted. The stationary part comprises the housing part and at least the first drive part(s).

The at least one transport protection element provides a releasable support or locking of the carrier part and/or transcutaneous device in the initial position, thereby preventing or limiting movement of the carrier part and/or transcutaneous device in the insertion direction and/or in the extraction direction opposite the insertion direction along the first axis. Thus, the transport protection elements may provide that the transcutaneous device in the initial position is substantially fixed or secured in relation to the carrier part thereby avoiding user discomfort or malfunction of the inserter system during use. Further, the transport protection element(s) may provide fixation of the carrier part and/or the transcutaneous device in relation to the stationary part reducing or eliminating the risk of breaking the seal or cover sheet during transportation.

The at least one transport protection element may comprise at least one bridge between the carrier part and the stationary part of the inserter system. The at least one bridge has dimensions or weakened sections that enable a user to break the bridges when loading the inserter system in order to move the carrier part to the first position in relation to the stationary part. At the same time, the bridge dimensions are selected to withstand forces resulting from transport bumps or shocks, thereby securing the carrier part in the initial position.

A bridge may comprise one or more weakened sections. A weakened section may have a minimum width in the range from about 0.1 mm to about 2.0 mm, such as in the range from 0.3 mm to 1.5 mm, e.g. about 1.0 mm. A weakened section may have a minimum thickness in the range from about 0.1 mm to about 2.0 mm, such as in the range from 0.3 mm to 1.5 mm, e.g. about 0.5 mm. A weakened section of a bridge may have a minimum cross sectional area in the range from 0.1 mm$^2$ to about 4.0 mm$^2$, such as in the range from about 0.3 mm$^2$ to about 2.0 mm$^2$, e.g. 0.5 mm$^2$, 0.8 mm$^2$ or 1.0 mm$^2$ The first unit may be made of a suitable polymer material such as polyoxymethylene (POM).

The at least one transport protection element may comprise a locking member detachably mounted in the housing. The locking member may engage with or supporting on the carrier part and/or a stationary part of the inserter system, such that movement of the carrier part in a direction, e.g. the insertion direction and/or the extraction direction, along the first axis in relation to the stationary part is limited or substantially prevented, thereby supporting the carrier part in the initial position. The locking member may limit or substantially prevent movement of the transcutaneous device in the extraction direction and/or in the insertion direction.

The at least one transport protection element may comprise at least one support element formed in the lid part. The at least one support element may include a first support element for supporting the carrier part and the transcutaneous device in the initial position. The first support element may have a first end positioned adjacent to the proximal surface of the transcutaneous device limiting or substantially preventing movement of the transcutaneous device in the insertion direction.

A first support element may be formed as a cylindrical tube having a first end and a suitable cross section, such as circular with a first diameter $d_1$, rectangular, oval, or any other suitable shape. The first support element may extend perpendicular to the first axis. The first support element may be arranged to support the transcutaneous device in the initial position by the first end of the first support element forming a stop member in the insertion direction. The distance between the first end of the first support element and the proximal surface of the transcutaneous device should be small enough to prevent displacement of the transcutaneous device in relation to the carrier part and/or the stationary part in the insertion direction prior to use, e.g. during storage or transportation. The distance between the first end of the first support element and the proximal surface of the transcutaneous device may be less than 2 mm, such as less than 1 mm.

The at least one support element may comprise one or more rods or plate structures, each having an end or edge adjacent to or contacting the transcutaneous device for preventing displacement of the transcutaneous device in relation to the carrier part and/or the stationary part in the insertion direction prior to use.

Figure 2:
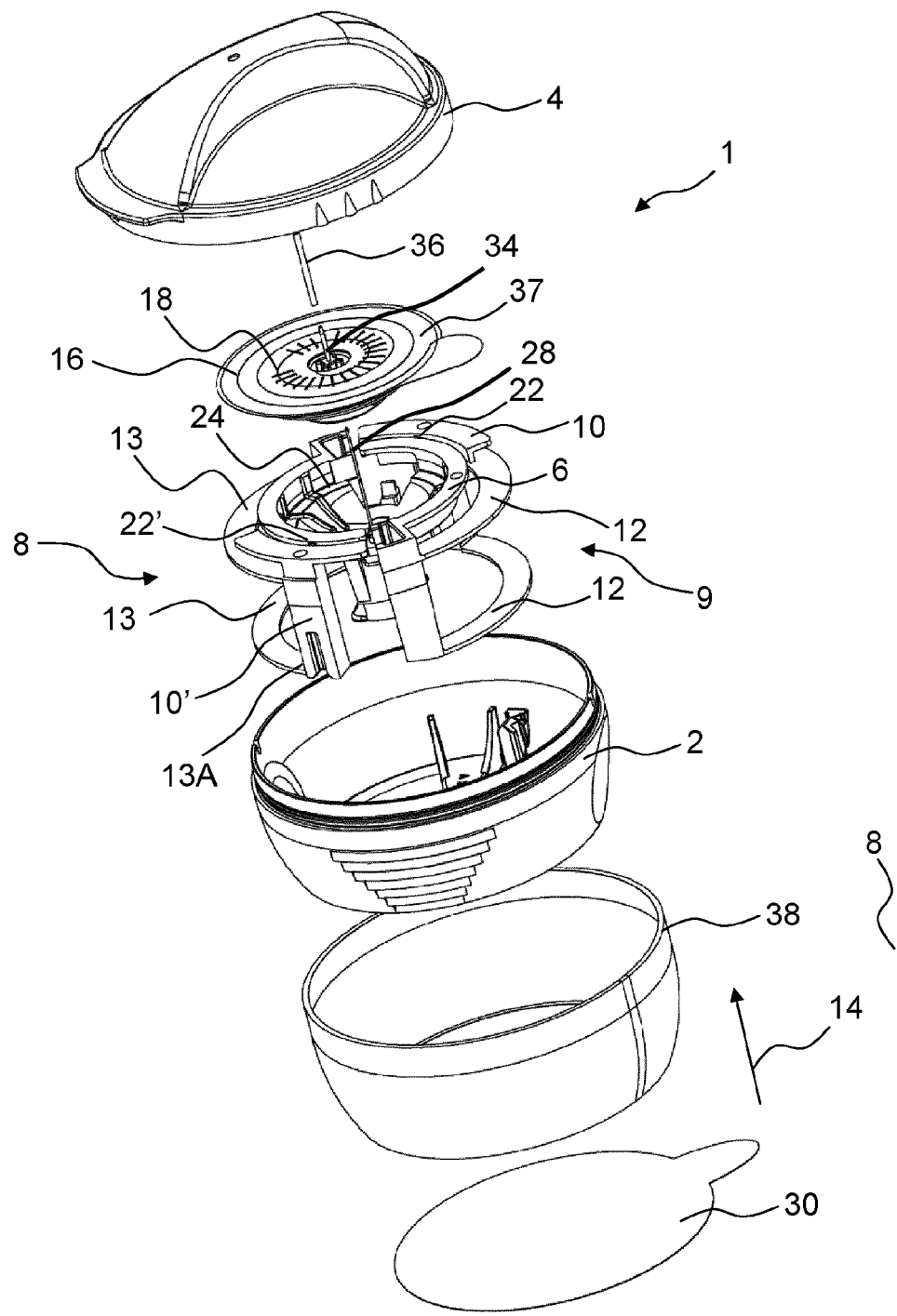
FIG. 2 is a different exploded view of the inserter system in FIG. 1.
Figure 3:
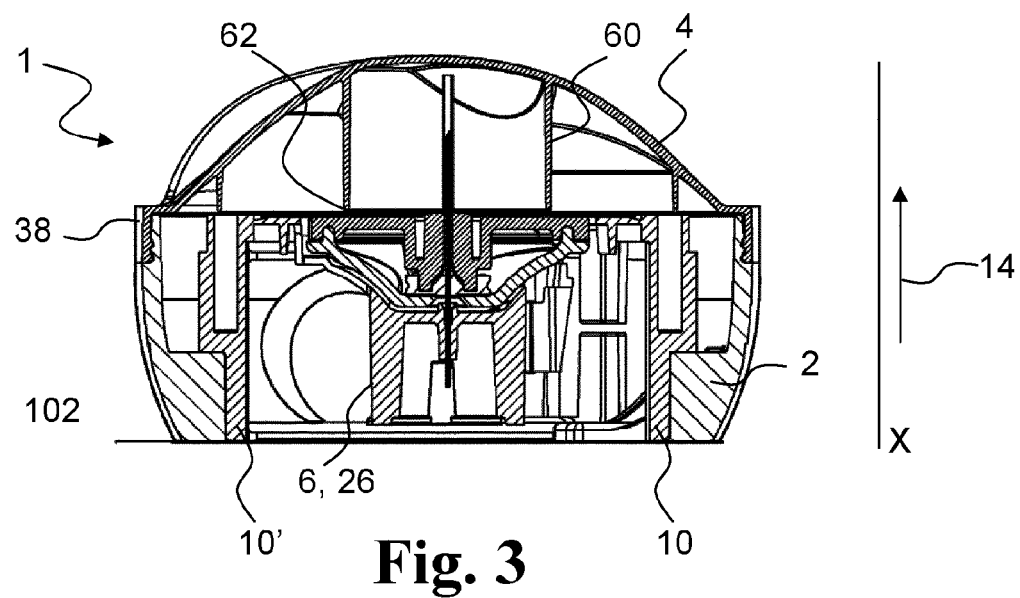
FIG. 3 shows a cross section of the inserter system in FIG. 1.
Figure 4:
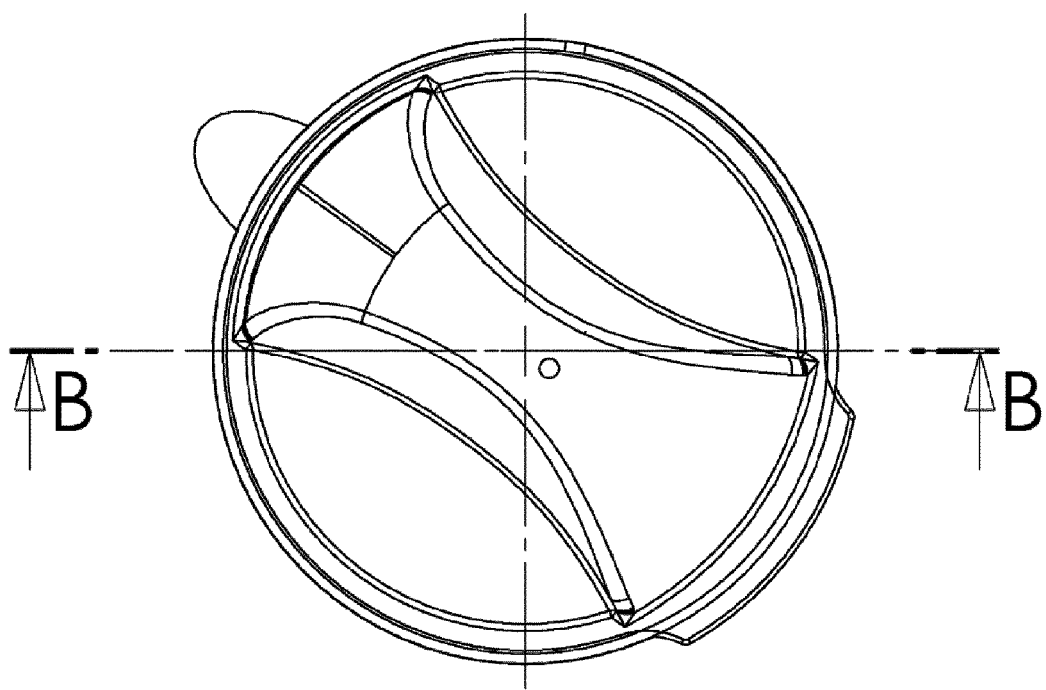
FIG. 4 shows the inserter system of FIG. 1 perpendicular to the insertion direction.

In the initial position of the carrier part, the drive unit may be unbiased FIGS. 1 and 2 show exploded views of an exemplary inserter system of the present invention and FIG. 3 illustrates a cross section of the inserter system 1 along the line B in FIG. 4. The inserter system 1 comprises a housing part 2 having a sidewall 2' with a first opening 2A at a first end and a second opening 2B at a second end. The inserter system 1 optionally comprises a lid part 4 covering the first opening 2A. Further, the inserter system comprises a carrier part 6 in an initial position in the housing 4 and a drive unit 8 comprising a first drive part attached to the housing. The carrier part 6 and the drive unit 8 form a first unit 9. The carrier part 6 comprises a handle portion 7 for enabling a user to manually load the inserter system by moving the carrier part in the retraction direction opposite the insertion direction 14. The first drive part comprises a first primary drive part 10 and a first secondary drive part 10'. Each first drive part 10, 10' comprises assembly means including an assembly recess 11, 11', respectively, for engaging with corresponding assembly means formed as assembly protrusions in the housing part 2 for mounting the first unit 9 in the housing part 2. The drive unit 8 comprises at least one spring element including two first spring elements in the form of leaf spring elements 12 which at their first ends 12A are connected to the first primary drive part 10 and at their second ends 12B are connected to the carrier part 6. Further, the drive unit 8 comprises two second spring elements in the form of leaf spring elements 13 which at their first ends 13A are connected to the first secondary drive part 10' and at their second ends 13B are connected to the carrier part 6. A configuration with a single spring element such as a helical spring element optionally in combination with guiding means for the carrier part is contemplated. The drive unit 8 is configured for moving the carrier part 6 from a first position to a second position in relation to the housing in an insertion direction 14 along the first axis. The inserter system 1 comprises a transcutaneous device 16 having a base 17 with a proximal surface 18 and a distal surface 20, wherein the transcutaneous device 16 is detachably attached to the carrier part 6 comprising a needle hub 24 including a hub base 26 and optionally an insertion needle 28. The transcutaneous device 16 comprises a transcutaneous element, such as a cannula 34 and/or a sensor element, mounted to the base 17 extending from the proximal surface facing the skin of a patient. The transcutaneous device may comprise a mounting pad 35 secured to the base 17 and having an adhesive proximal surface for securing the transcutaneous device to a base plate and/or on the skin of the patient. A removable protective layer or sheet 37 covers the adhesive surface.

The inserter system 1 comprises at least one transport protection element in the form of a first bridge 22 connecting the first primary drive part 10 and the carrier part 6 in the initial position. Further, the inserter system 1 comprises a second bridge 22' connecting the first secondary drive part 10' and the carrier part 6 in the initial position. A user loading the inserter system breaks the transport protection elements, i.e. bridges 22, 22', when moving the carrier part from the initial position to the first position in relation to the housing. The bridges 22, 22' are molded as a part of the single unit 9 made of POM. The bridges 22, 22' each comprise a weakened section having a minimum width of about 1.0 mm and a minimum thickness of about 0.5 mm for having desired strength to withstand transport shocks and at the same time enabling a user to break the bridges when loading the inserter system.

The housing part 2 comprises a first projecting element 40 and a second projecting element 42 extending from the sidewall 2' and forming a support surface for engagement with locking members 50, 52 of the carrier part 6 for releasably locking the carrier part 6 with the transcutaneous device 16 in the first position.

The at least one transport protection element comprises at least one support element including a first support element 60 formed in the lid part 4 of the inserter system 1. The first support element 60 is formed as a cylindrical tube having a first end 62 and a circular cross section with a first diameter $d_1$, the cylindrical tube extending perpendicular to the first axis. The first support element 60 is arranged to support the transcutaneous device 16 in the initial position by the first end 62 forming a stop member in the insertion direction. The distance between the first end 62 of the first support element 60 and the protective sheet 37 of the transcutaneous device should be small enough, such as less than 2.0 mm, to prevent displacement of the transcutaneous device 16 in relation to the carrier part 6 in the insertion direction prior to use, e.g. during storage or transportation. In one or more embodiments, the first end 62 contacts the protective sheet 37. The at least one support element may comprise one or more rods or plate structures, each having an end or edge adjacent to or contacting the transcutaneous device.

The inserter system 1 optionally comprises a packing film 38 that is shrink-fitted around the housing part and the lid part 4. The packing film 38 is used for showing if the inserter system has been tampered with and therefore may not be sterile.

Figure 5:
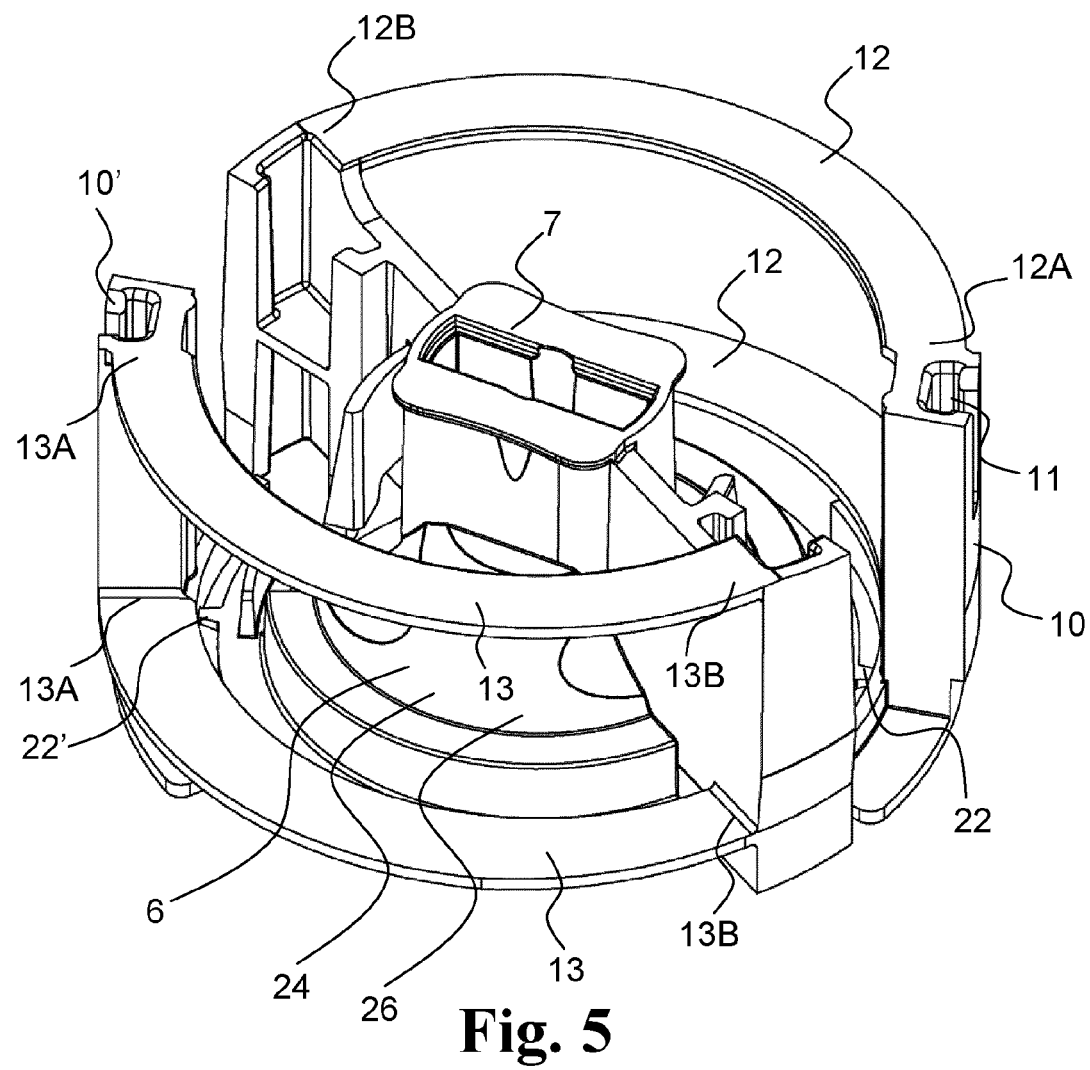
FIG. 5 shows a perspective view of a first unit of an inserter system.
Figure 6:
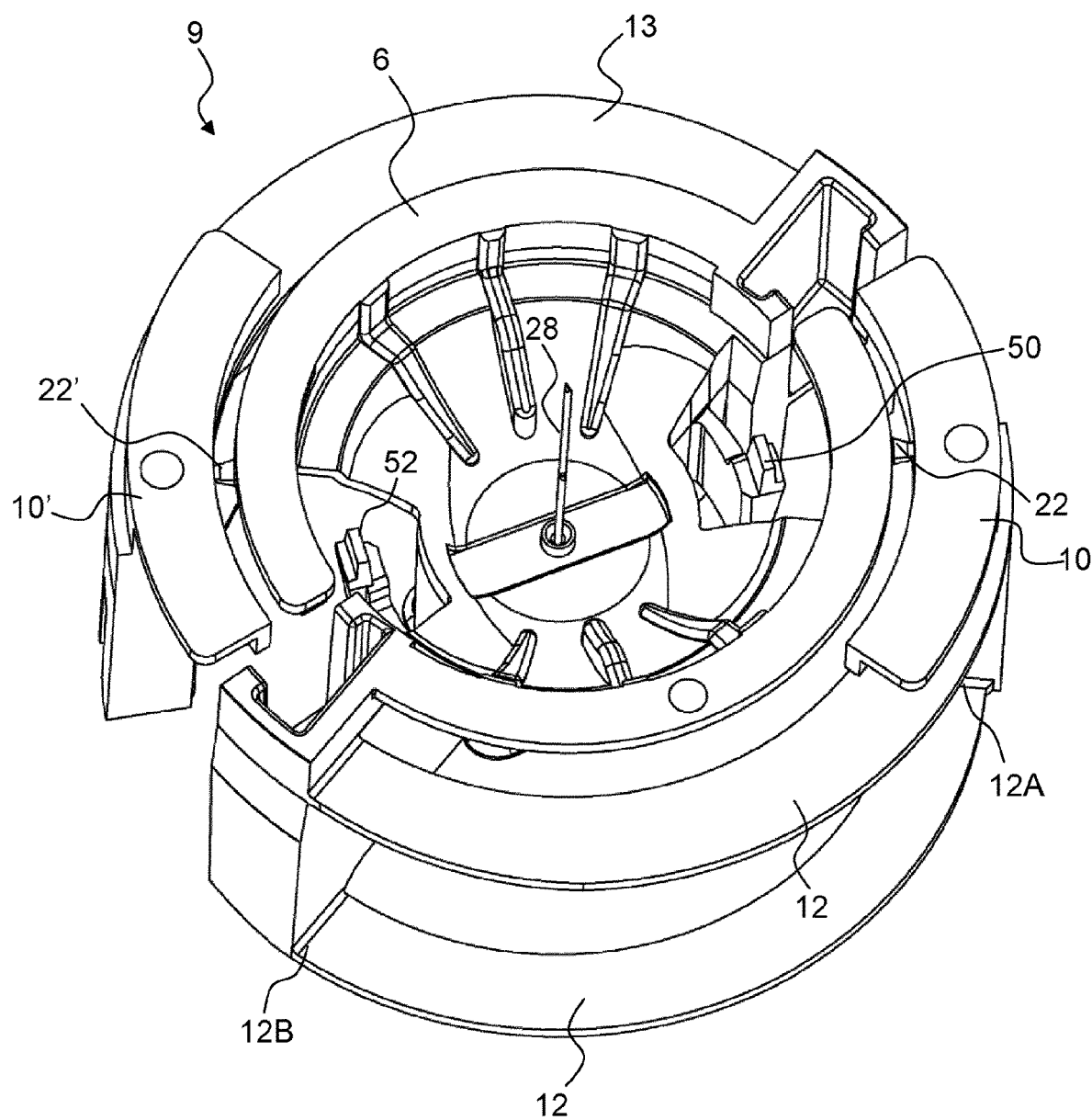
FIG. 6 shows another perspective view of the first unit in FIG. 5.

FIGS. 5 and 6 show different perspective views of the first unit 9 comprising the carrier part 6 and the drive unit 8. The carrier part 6 comprises a first primary locking element 50 and a second locking element 52 for releasably locking the carrier part 6 in the first position by supporting on the projecting elements 40, 42. Alternatively, or in combination, first locking members may be configured to support on first drive part(s) of the drive unit for releasably locking the carrier part in the first position. The locking elements are released by manual deformation of the housing part 2.

Figure 7:
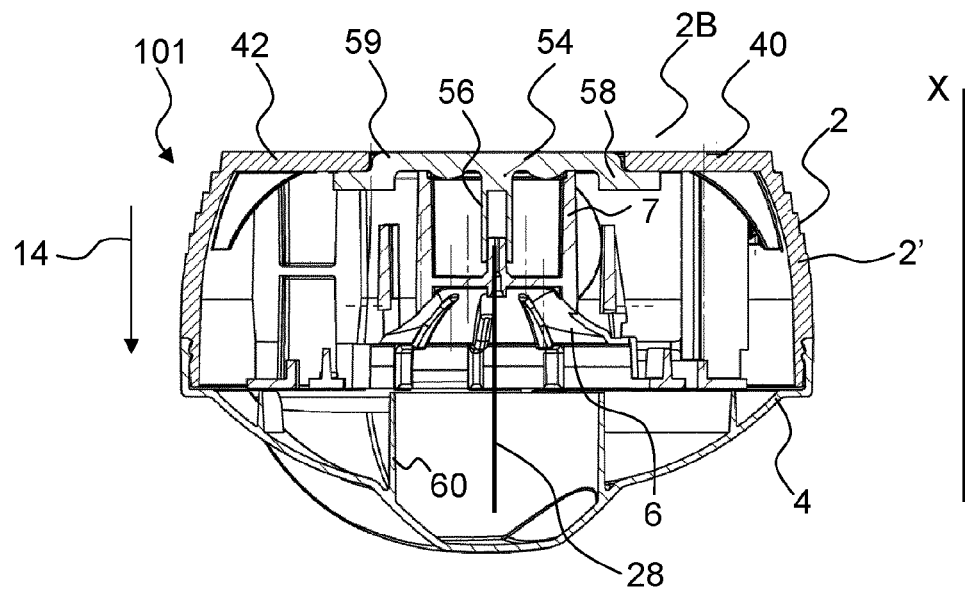
FIG. 7 shows a cross section of an inserter system.
Figure 8:
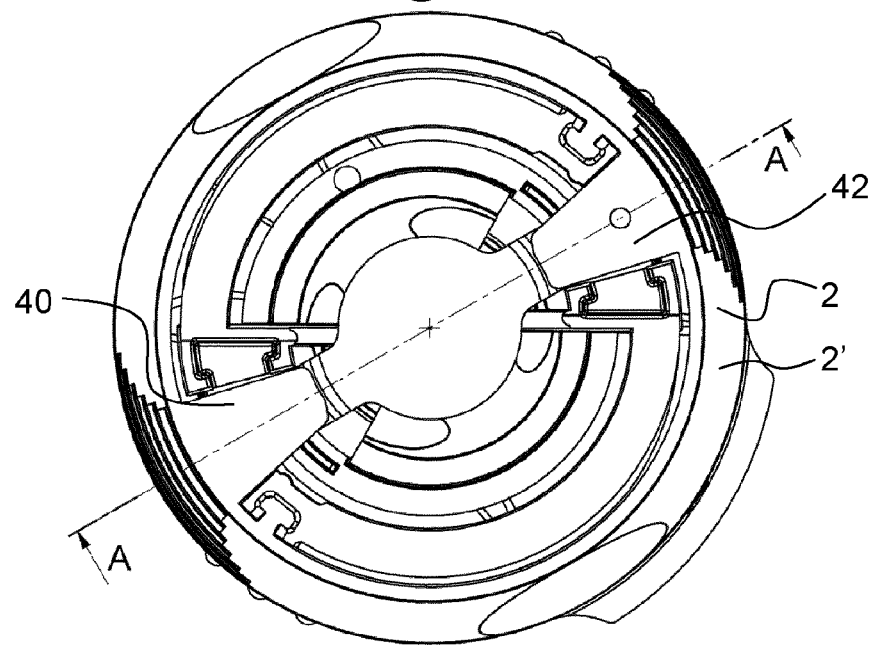
FIG. 8 shows the inserter system of FIG. 7.
Figure 9:
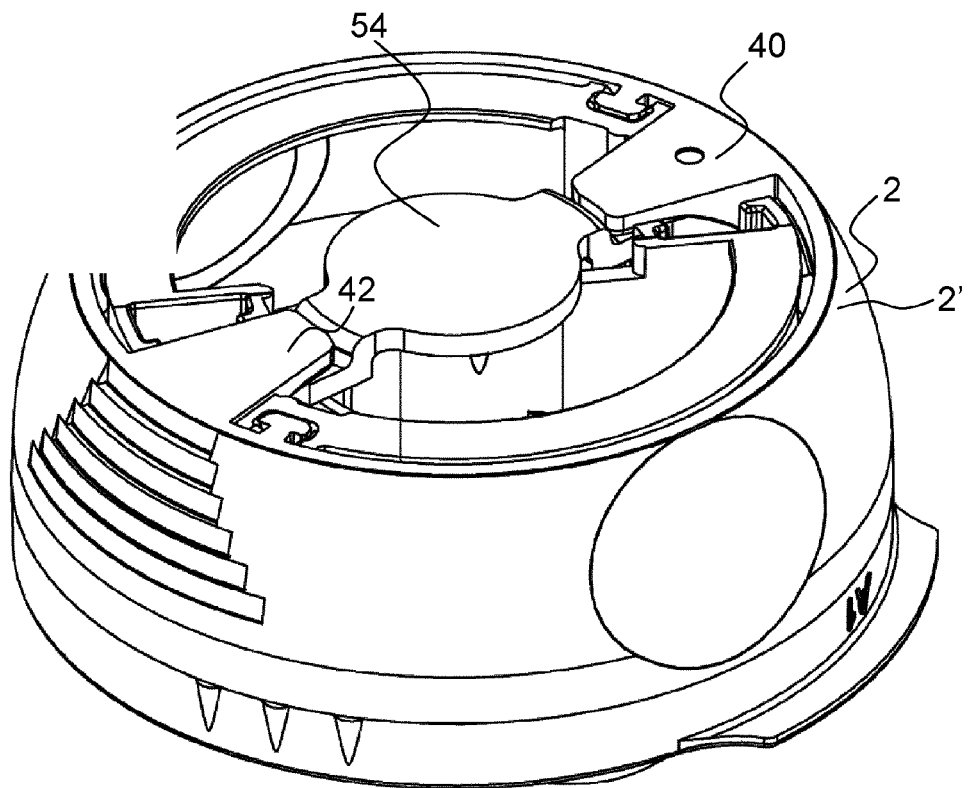
FIG. 9 shows a perspective view of the inserter system in FIG. 7.

FIGS. 7-9 show an inserter system 101 without a transcutaneous device. The inserter system 101 comprises a locking member 54 detachably mounted in the housing part 2. The locking member 54 comprises a first part 56 extending along the first axis X and in the initial position engaging with the handle portion 7 of the carrier part 6. The handle portion 7 forms a cavity, e.g. with rectangular cross section perpendicular to the first axis, for accommodating and supporting the first part 56. Further, the locking member 54 comprises at least one second locking element including a second primary locking element 58 and a second secondary locking element 59 extending perpendicularly to the first axis and supporting on the stationary part (projecting elements 40, 42) of the inserter system 101. Thereby, the carrier part 6 is prevented from moving in the retraction direction in the initial position such that the cover sheet 30 is not damaged by the carrier part moving due to bumps and shocks during transport. In one or more embodiments, the second locking element(s) 58, 59 may be arranged for preventing the carrier part from moving in the insertion direction in the initial position, e.g. by extending into one or more recesses in the stationary part. The locking member 54 may comprise a third locking element (not shown) configured for engaging and locking the carrier part to the locking member 54. The locking member 54 is released by manual rotation, e.g. 90°, of the locking member around the first axis.

Figure 10:
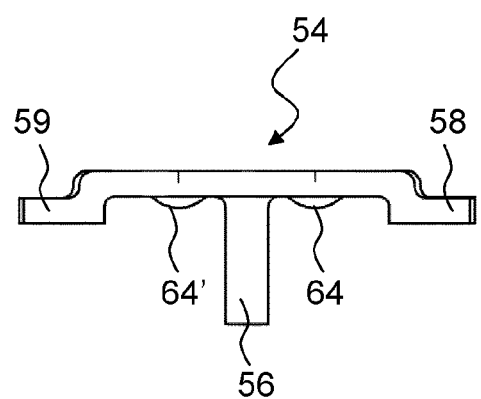
FIG. 10 shows a locking member.

FIG. 10 is a cross sectional view of the locking member 54. The locking member 54 comprises at least one holding element 64, 64' for supporting the locking member in the initial position by extending into the cavity of the handle portion 7 preventing unintentional rotation of the locking member 54 when the inserter system is assembled. When the locking member 54 is rotated by a user, the carrier part 6 is forced slightly in the insertion direction by the holding elements 64, 64'. The locking member 54 is prevented from rotating in the locked initial position, when the lid part 4 with the first support element 60 is assembled with the housing part 2.

LIST OF REFERENCES 1, 101 Inserter system
2 Housing part
2' Sidewall
2A First opening
2B Second opening
4 Lid part
6 Carrier par
7 Handle portion
8 Drive unit
9 First unit
10 First primary drive part
10' First secondary drive part
12 First spring element
12A First end
12B Second end
13 Second spring element
13A First end
13B Second end
14 Insertion direction
16 Trancutaneous device
17 Base
18 Proximal surface
20 Distal surface
22 First bridge
22' Second bridge
24 Needle hub
26 Hub base
28 Insertion needle
30 Seal/cover sheet
34 Cannula
35 Mounting pad
36 Needle protector
37 Protective sheet
38 Packing film
40 First projecting element
42 Second projecting element
50 First primary locking element
52 First secondary locking element
54 Locking member
56 First part
58 Second primary locking element
59 Second secondary locking element
60 First support element
62 First end
64, 64' Holding element
X First axis

The invention claimed is:

1. An inserter system comprising:
a housing;
a carrier movably mounted in the housing, wherein the carrier is movable relative to the housing in a first axial direction from an initial position to a retracted position, and in a second axial direction from the retracted position to an insertion position, the first axial direction opposite the second axial direction;
a driver mounted in the housing, wherein the driver is operable to move the carrier from the retracted position to the insertion position;
a transcutaneous device attached to the carrier; and
a breakable bridge engaged between the carrier and a portion of the driver when the carrier is in the initial position to thereby support the carrier in the initial position, wherein the breakable bridge is configured to break in response to movement of the carrier from the initial position to the retracted position.

2. The inserter system of claim 1, further comprising at least one locking member configured to selectively limit movement of the transcutaneous device.

3. The inserter system of claim 2, wherein the at least one locking member comprises a first locking member and a second locking member operable to engage the first locking member;
wherein the housing comprises the first locking member; and
wherein the carrier comprises the second locking member.

4. The inserter system of claim 1, further comprising a gas permeable seal or cover sheet.

5. The inserter system of claim 1, wherein the transcutaneous device is detachably attached to the carrier part.

6. An inserter system comprising:
a housing having an open proximal end;
a carrier movably mounted in the housing, wherein the carrier is movable from an initial position to a retracted position, and from the retracted position to an insertion position;
a transcutaneous device attached to the carrier, wherein movement of the carrier from the retracted position to the insertion position moves a portion of the transcutaneous device beyond the proximal end of the housing;
a gas permeable seal or cover sheet covering the open proximal end of the housing; and
a locking member configured to selectively retain the carrier in the initial position to thereby discourage damaging of the gas permeable seal or cover sheet by the carrier and/or the transcutaneous device.

7. The inserter system of claim 6, further comprising a driver mounted in the housing, wherein the driver is operable to move the carrier from the retracted position to the insertion position.

8. The inserter system of claim 7, further comprising a breakable bridge positioned between the carrier and a portion of the driver when the carrier is in the initial position to thereby support the carrier in the initial position.

9. The inserter system of claim 6, wherein the gas permeable seal or cover sheet allows for sterilization of the inserter system.

10. The inserter system of claim 6, further comprising a support configured to limit movement of the transcutaneous device relative to the carrier.

* * * * *